United States Patent [19]

Nelson et al.

[11] Patent Number: 4,580,897
[45] Date of Patent: Apr. 8, 1986

[54] CENTRIFUGAL ANALYZER ROTORS

[75] Inventors: Larry A. Nelson; Gregory C. Healey, both of Spokane, Wash.

[73] Assignee: Allied Corporation, Morristown, N.J.

[21] Appl. No.: 615,644

[22] Filed: May 31, 1984

[51] Int. Cl.⁴ .......................................... G01N 21/07
[52] U.S. Cl. .................................. 356/246; 356/427; 422/64
[58] Field of Search ....................... 356/246, 427, 440; 422/64, 72; 436/45

[56] References Cited

U.S. PATENT DOCUMENTS

| | | | |
|---|---|---|---|
| 3,586,484 | 6/1971 | Anderson | 23/230 |
| 3,759,666 | 9/1973 | Hill | 23/230 |
| 3,798,459 | 3/1974 | Anderson | 250/218 |
| 3,813,031 | 5/1974 | Anderson | 233/26 |
| 3,873,217 | 3/1975 | Anderson | 356/246 |
| 3,899,296 | 8/1975 | Mailen | 23/259 |
| 4,123,173 | 10/1978 | Bullock | 356/246 |
| 4,226,531 | 10/1980 | Tiffany | 356/246 |
| 4,314,970 | 2/1982 | Stein et al. | 422/72 |
| 4,373,812 | 2/1983 | Stein | 356/246 |
| 4,519,981 | 5/1985 | Guigan | 356/246 X |

Primary Examiner—Vincent P. McGraw
Assistant Examiner—Robert D. V. Thompson, III
Attorney, Agent, or Firm—Lowell H. McCarter

[57] ABSTRACT

A multicuvette rotor for use in a centrifugal analyzer defines a circumferential array of elongated radially extending cuvettes. Each elongated cuvette defines a first chamber for receiving a first reactant and a loading port through which the first reactant is introduced into the first chamber region, a second chamber region for receiving a second reactant and a loading port through which the second reactant is introduced into the second chamber region, and divider structure between the first and second chamber regions that has a ramp surface and a ramp crest spaced from the ceiling surface of the cuvette so that a transfer passage between the first and second chamber regions is defined through which the first reactant may be flowed into the second chamber region for forming a reaction product with the second reactant. Deflector structure extends downwardly from the cuvette ceiling surface adjacent each second loading port, each deflector structure being located radially outwardly from a line extension of the ramp surface and having a lower end substantially in alignment with the ramp crest. An analysis region is defined adjacent the radially outer wall of the cuvette where the resulting reaction product is subjected to analysis.

24 Claims, 9 Drawing Figures

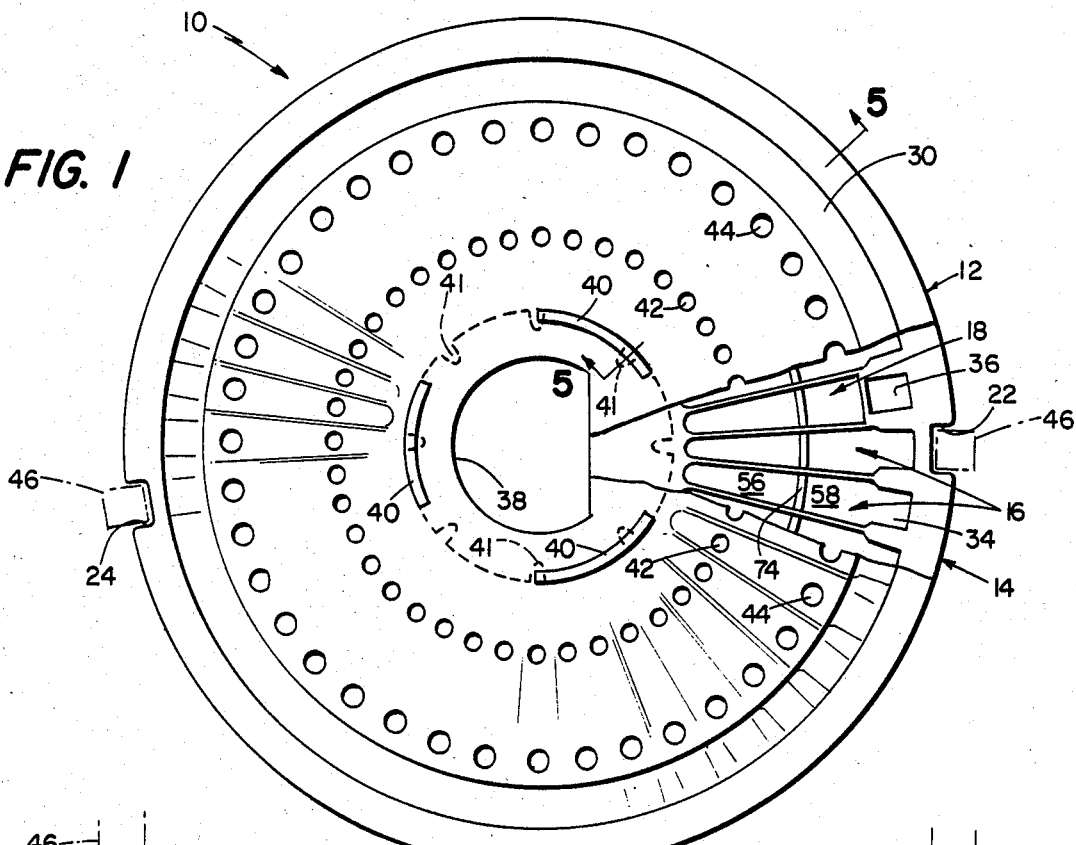
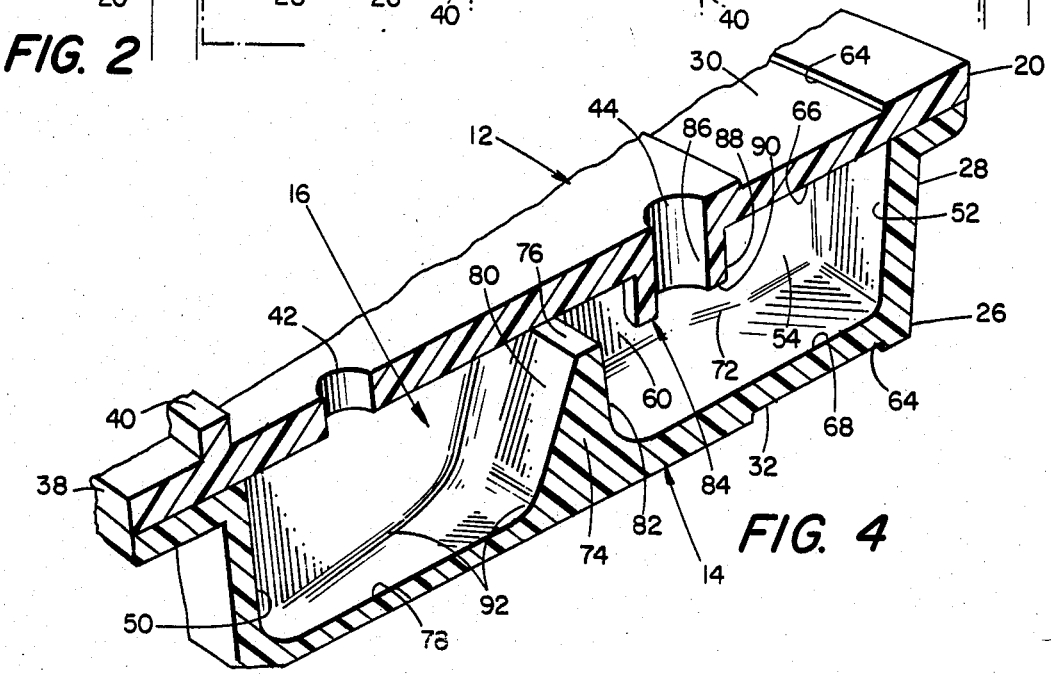

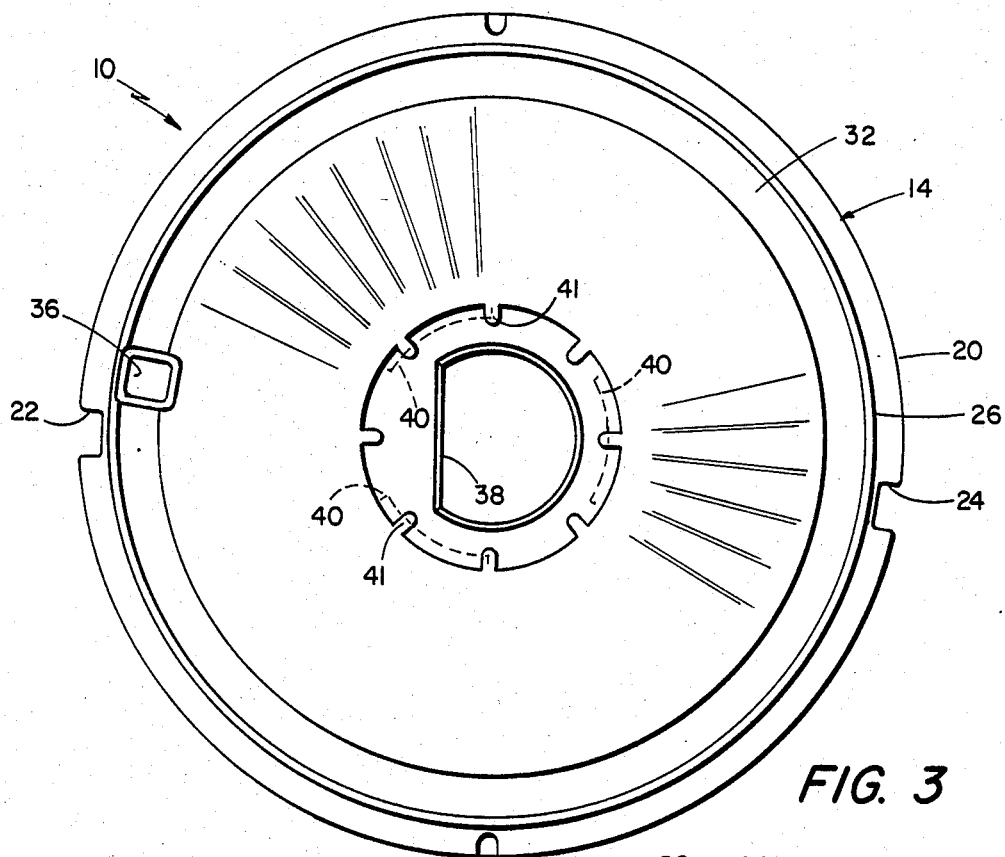
FIG. 3
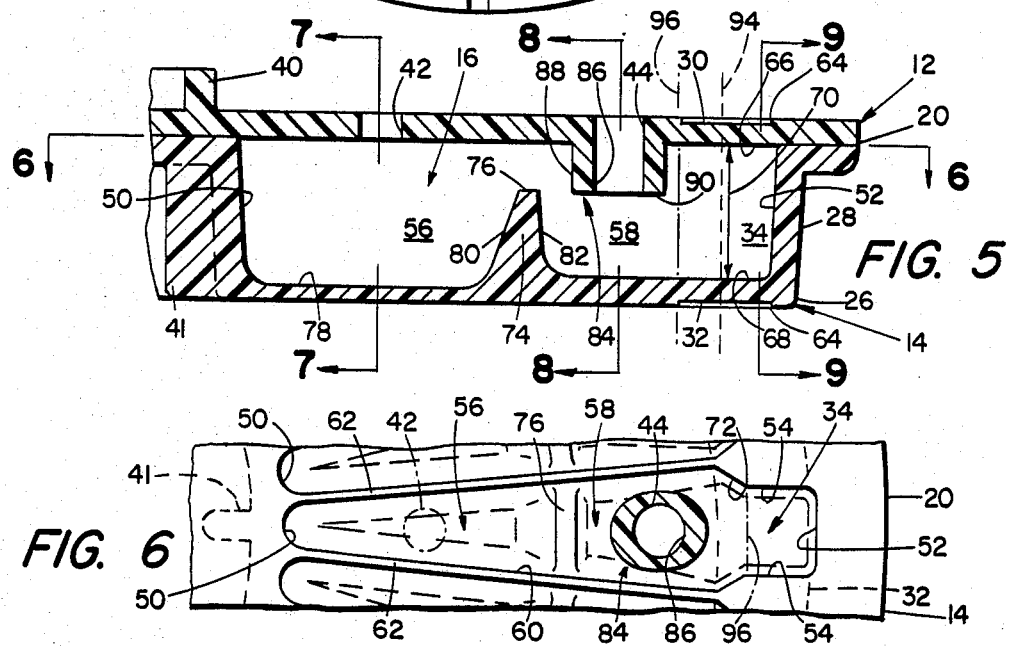
FIG. 5
FIG. 6
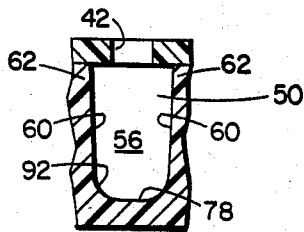
FIG. 7
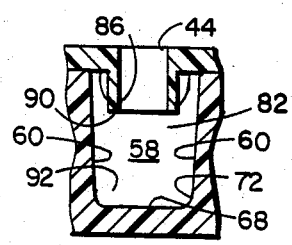
FIG. 8
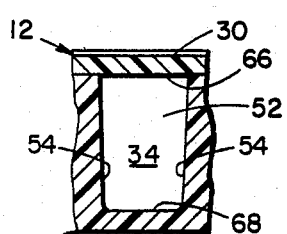
FIG. 9

CENTRIFUGAL ANALYZER ROTORS

This invention relates to analytical systems, and more particularly to cuvette rotors for use in automated centrifugal analyzer systems and the like.

Centrifugal analyzers are useful in performing a variety of analyses, including kinetic and endpoint analyses, by such techniques as absorption, light scattering and fluorescence. In general, such analyzers utilize a multicuvette rotor assembly which has a circumferential array of spaced elongated radially extending cuvettes, each of which has an inner chamber for initially holding a first reactant which frequently is a sample of blood or other biological fluid, and an outer chamber for initially holding one or more different reactants. Divider structure such as a ramp separates the two chambers, and reactants are transferred by centrifugal force to an analysis region at the outer end of the cuvette for mixing and reaction and subsequent analysis of the reaction by photometric or other analysis technique.

Such rotors may be of the reusable type, as disclosed in Stein et al. U.S. Pat. No. 4,314,970 for example or of the disposable type as disclosed in Tiffany et al. U.S. Pat. No. 4,226,531 for example. The rotor disclosed in each of these patents has twenty cuvettes that are loaded successively with automated loading equipment, small quantities of sample plus optional quantities of diluent and second reagent (volumes in the range of 2-100 microliters) typically being loaded into the inner chambers and reagents in quantities of up to two-hundred microliters being loaded into the outer chambers. The loaded cuvette rotor is then transferred to an analyzer for photometric and/or fluorescence analysis. In a typical analysis sequence, the rotor assembly is accelerated to about 4,000 rpm in about one second for combining sample and reagent, then braked for further mixing, and then brought up to about a speed of about 1,000 rpm for analysis.

Such analyzers are commonly used in the analysis of biological fluids such as blood, blood plasma or serum components, and perform absorbance mode analyses for glucose, cholesterol, creatinine, total protein, calcium, phosphorous, enzymes, and the like, and fluorescence or light scattering mode analyses for glucose, bile acids, phenytoin, theophylline, gentamycin and the like. To achieve desired analysis accuracies, the rotor must have precise and stable dimensional accuracies that are uniform between the several cuvettes of the rotor, and particularly in the analysis region between upper and lower windows at the outer end of each of the cuvettes.

Reusable rotors are difficult to clean adequately and to safeguard against possibilities of error from cross-contamination and the like. For these reasons single use disposable rotors of the type shown in the above-mentioned Tiffany patent are frequently used. Such rotors are of compact size (about ten centimeters in diameter) and are composed of cover and body members that are permanently joined by ultrasonic welding to individually seal the twenty cuvettes. The invention, in one aspect, provides a similar single use cuvette rotor which has a larger number of cuvettes so that the cost per test can be reduced and the throughput of the analyzer can be increased, each cuvette accommodating the range of reagent and sample volumes that are required to perform a range of analyses and providing both adequate isolation between chamber compartments to avoid an unacceptable tendency of reagent material to spontaneously move or "wick" from one chamber compartment to the other, resulting in premature mixing of the reactants, and rapid and effective mixing of reactants when the rotor is spun and braked prior to analysis.

In accordance with another aspect of the invention, there is provided a multicuvette rotor for use in a centrifugal analyzer in which a circumferential array of elongated radially extending cuvettes are defined. Each elongated cuvette defines a first chamber for receiving a first reactant and a loading port through which the first reactant is introduced into the first chamber region, a second chamber region for receiving a second reactant and a loading port through which the second reactant is introduced into the second chamber region, and divider structure between the first and second chamber regions that has a ramp surface and a ramp crest spaced from the ceiling surface of the cuvette so that a transfer passage between the first and second chamber regions is defined through which the first reactant may be flowed into the second chamber region for forming a reaction product with the second reactant. Deflector structure extends downwardly from the cuvette ceiling surface adjacent each second loading port, each deflector structure being located radially outwardly from a line extension of the ramp surface and having a lower end substantially in alignment with the ramp crest. An analysis region is defined adjacent the radially outer wall of the cuvette where the resulting reaction product is subjected to analysis.

In accordance with another aspect of the invention, there is provided a multicuvette rotor for use in a centrifugal analyzer in which a circumferential array of elongated radially extending cuvettes are defined. Each elongated cuvette defines a first chamber for receiving a first reactant and a loading port through which the first reactant is introduced into the first chamber region, a second chamber region for receiving a second reactant and a loading port through which the second reactant is introduced into the second chamber region, and divider structure between the first and second chamber regions defines a transfer passage through which the first reactant may be flowed into the second chamber region for forming a reaction product with the second reactant. An analysis region is defined adjacent the radially outer wall of the cuvette where the resulting reaction product is subjected to analysis. Spacer projection structure in at least one surface of the rotor permits a plurality of the rotors to be stacked in spaced alignment and the cuvettes maintained in stable thermal equilibrium by flow of equilibrating fluid over the spaced exterior surfaces of the rotors in the stack. In preferred embodiments, the spacer projection structure includes spaced arcuate portions that project upwardly from the upper surface of the rotor. The rotor further preferably includes an alignment recess in the periphery of said rotor that permit a plurality of said rotors in said stack to be positioned in angular alignment, and in a particular embodiment the rotor has a peripheral flange and two of the alignment recesses are in that flange and offset from diametrically opposite relation to one another by at least one cuvette.

In preferred embodiments, the second chamber defining structure has generally vertical outwardly diverging sidewall surfaces in the vicinity of the deflector structure, the analysis region defining structure has generally vertical parallel sidewall surfaces, and inwardly converging generally vertical transition surfaces are provided between the sidewall surfaces of the second chamber and the analysis region.

In a particular embodiment, the rotor assembly has a diameter of about ten centimeters and an overall height of about one centimeter, and defines thirty-nine analysis cuvettes. The loading ports for the inner cuvette chambers are in a circumferential array and the loading ports for the outer cuvette chambers in an outer circumferential array. Three arcuate spacer projections, each of about 60 degrees angular length, in the upper surface of the rotor assembly and alignment recesses in its peripheral flange permit the rotors to be positioned in stacked, spaced, angular alignment and the cuvettes to be maintained in stable thermal equilibrium by the flow of equilibrating fluid over the exterior surfaces of the rotors in the stack. Each cuvette of that rotor has a length of about three centimeters; its planar top (ceiling) and bottom (floor) walls are spaced apart about ¾ centimeter in the analysis and second compartment regions and about 0.8 millimeter apart in the first compartment region; the side walls of the first and second compartment regions diverge outwardly while the analysis region side walls are parallel; and the adjacent cuvettes are separated by solid radial webs. The rotor has a continuous cylindrical outer wall that defines a series of optical cuvette end windows that are transparent at analytical wavelengths.

The divider structure has a steeply inclined ramp surface (preferably at an angle of less than thirty degrees from the vertical) and its crest height is greater than half the distance between the ceiling and floor surfaces of the cuvette. The deflector structure in that embodiment is a channel extension of the second loading port with an outer surface of elliptical configuration and extends down from the ceiling surface a distance greater than one-fourth of the total height of the cuvette chamber in that region with the lower surface edge of the deflector located substantially in alignment with the ramp crest. The length of the optical path in the analysis region is greater than the circumferential width or radial length of the analysis region and the volumes of both the first and second chambers are greater than that of the analysis region. The first compartment has greater chamber height than the second compartment. Both the upper and lower optical windows are aligned annular optical recesses with an inner radius of about four centimeters, a width of about five millimeters and a depth of about one-fourth millimeter. The planar floor surface of each window recess has an optical finish better than three microinches, with similar quality optical surfaces on the inner surfaces of the analysis region and surfaces of the cuvette end windows while other surfaces of the cuvette compartments have greater roughness that is effective to retard wicking tendencies.

The invention provides compact, economical centrifugal analyzer rotors that may be of the single use type with capability for increased throughput and reduced cost per analysis and compatibility with automated rotor handling equipment.

Other features and advantages of the invention will be seen as the following description of a particular embodiment progresses, in conjunction with the drawings, in which:

FIG. 1 is a top plan view (with portions broken away) of a multicuvette rotor assembly in accordance with the invention;

FIG. 2 is a side view (with portions broken away) of the rotor assembly shown in FIG. 1, together with additional rotors (shown in chain line) in stacked relationship;

FIG. 3 is a bottom view of the rotor assembly shown in FIG. 1;

FIG. 4 is a sectional perspective view showing details of a cuvette in the rotor assembly shown in FIG. 1;

FIG. 5 is a sectional view taken along the line 5—5 of FIG. 1; and

FIGS. 6–9 are sectional views taken along the lines 6—6, 7—7, 8—8 and 9—9 respectively of FIG. 5.

DESCRIPTION OF PARTICULAR EMBODIMENT

With reference to FIGS. 1–3, rotor assembly 10 has a diameter of about ten centimeters and an overall height of about 1¼ centimeters, and is formed of an injection-molded acrylic cover member 12 and an injection-molded acrylic body member 14 that are ultrasonically welded together, the body and cover members having appropriate transparency, chemical resistance, and optical characteristics for photometric analysis. Rotor assembly 10 defines a circumferential array of thirty-nine individual analysis cuvettes 16 (plus a reference region 18 of similar configuration) and has circumferential flange structure 20 at its periphery in which are formed alignment recesses 22, 24. A series of optical end windows 28, one for each cuvette 16, are formed by continuous circumferential surface 26 below flange lip 20. Annular optical window channel recess 30 (about ½ centimeter wide with its inner edge at about four centimeters radius) is formed in the upper surface of rotor assembly 10, and a corresponding continuous annular optical window channel recess 32 is formed in the lower surface of rotor 10, channels 30, 32 being aligned and defining cuvette analysis regions 34 therebetween. Socket recess 36 that interrupts lower channel 32, is aligned with reference region 18 and, when rotor 10 is seated on a drive table of the cooperating analyzer, a projection upstanding from the drive table which houses a temperature sensor is received in socket 36, thus providing coordinated features of accurate rotor alignment and temperature monitoring capability in the analysis region area during mixing and analysis.

Formed in cover member 12 (as indicated in FIG. 1) are a substantially D-shaped central opening 38, a series of three arcuate spacer ribs 40, a circumferential array of first loading ports 42, a second circumferential array of second loading ports 44, and annular recessed optical window channel 30 outwardly of ports 44 and adjacent rim 22. Rotors 10 may be stacked (as indicated diagrammatically in FIG. 2) with three arcuate ribs 40 (each of about sixty degrees angular extent) seating radial projections 41 in the body member 14 that surround opening 38 to provide vertical spacing; and alignment recesses 22, 24 (which are offset by one cuvette from diametrically opposed alignment) received in vertical guide members 46 for automated rotor handling.

The thirty-nine analysis cuvettes 16 are of the same configuration, and further details of a cuvette 16 may be seen with reference to FIGS. 4–6. Each cuvette 16 has a length of about three centimeters between cylindrical inner wall surface 50 and planar outer wall surface 52. Surface 52 has an optical surface finish of better than three microinches and defines the inner surface of optical window 28. Each cuvette 16 has substantially parallel side wall surfaces 54 (spaced about 0.5 centimeter apart) adjacent outer wall 52 that bound analysis region 34. Each cuvette 16 also has an inner chamber portion 56 (which is loaded through port 42) and an outer chamber portion 58 (which is loaded through port 44). The surfaces 60 of each cuvette that define the side walls of chambers 56 and 58 diverge at an angle of about nine degrees and are formed by solid webs 62 that are about one millimeter thick.

The two aligned optical window channels 30, 32 are each about ½ centimeter wide, with the outer edges 64 of channels 30, 32 located substantially in alignment with outer surface 52 of cuvette 16. The ceiling (upper) and floor (lower) surfaces 66, 68 in each analysis region 34 have optical finishes of better than three microinches (as have surfaces 30, 32 and 52) and are spaced about ¾ centimeter apart to provide an optical path 70 of about ¾ centimeter length in each analysis region. Thus, each analysis region 34 is bounded by parallel side surfaces 54 spaced about ½ centimeter apart and parallel top and bottom surfaces 66, 68 spaced about ¾ centimeter apart and has a radial length of about ½ centimeter with an effective volume of about one-hundred-fifty microliters. Short transition region wall surfaces 72 (inclined at a 30 degree angle) connect diverging side wall surfaces 60 of chamber 58 (spaced about 5.5 millimeters apart) and side wall surfaces 54 of analysis region 34.

As indicated in FIGS. 2 and 4–6, ramp structure 74 separates chambers 56 and 58 and extends between side walls 60. The crest 76 of divider ramp 74 has a radial width of about one millimeter and extends about five millimeters above surface 78 of chamber 56; a planar ramp surface 80 (inclined at an angle of twenty degrees to the vertical) that forms the rear wall of chamber 56; and a planar vertical surface 82 that forms the forward wall of chamber 58, so that chamber 56 has a static capacity of about three-hundred microliters and chamber 58 has a static capacity of about two-hundred-sixty microliters. Port 42 is spaced about 0.6 centimeter from cuvette wall 50, ramp crest 76 is spaced about 1.5 centimeters from wall 50; and port 44 is spaced about 20 centimeters from wall 50. Extending downwardly from cover surface 66 and radially outwardly from ramp 74 is deflector structure 84 that has an inner surface 86 that defines a passage extension of port 44 and an outer surface 88 of elliptical configuration (FIG. 6)—a length (major dimension) of about 0.45 centimeter and a width (minor dimension) of about 0.4 centimeter)—that is spaced about two millimeters from wall 82 of divider ramp 74. The lower surface 90 of deflector structure 84 is located substantially in alignment with (about ¼ millimeter below) ramp crest surface 76. As indicated in FIGS. 4–8, ramp 74 and chamber base surfaces 68, 78 are connected to the adjacent side walls 62 by curved areas 92 (of about 1.5 millimeter radius) that provide smooth and gradual transition surfaces effective to retard premixing due to spontaneous capillary flow of reagent materials along those surface intersections from one chamber to the other over barrier ramp 74.

In use, a stack of rotor assemblies 10 may be initially disposed in aligned orientation (as indicated in FIG. 2) with notches 22, 24 in vertical aligning members 46 and with the upper surface of each rotor spaced from the bottom surface from the rotor immediately above in the stack by spacer webs 40 on which are seated projections 41 so that substantially the entire external surfaces of the cuvette chambers may be exposed to flow of equilibrating fluid. The rotors 10 are successively fed from the stack to a loading station where the chambers 56, 58 of some or all of the cuvettes 16 are loaded with appropriate reagent and sample materials in conventional manner, one dispensing pipette being inserted through port 44 and deflector structure 84 into chamber 58 and a second dispensing pipette being concurrently inserted through port 42 into chamber 56. After loading, the rotor is transferred to a rotor drive table of a centrifugal analyzer where an aligning projection stub which carries a temperature sensor is inserted into socket 36 as rotor 10 is seated on the table.

In an analysis sequence, rotor 10 is accelerated to about 4000 rpm during a preliminary run to flow reactant materials contained in the inner chambers 56 up the seventy degree ramp surfaces 80 and radially outwardly across ramp crests 76. Those materials flow upwardly and radially outwardly from the ramp crests 76, and are diverted in diverging action around the deflectors 84 and then in converging action by transition surfaces 72 for combining with reactant materials that have been similarly accelerated from the outer chambers 58 into the analysis regions 34. This flow of the stream of reactant material from the inner chambers 56 is above the lower surfaces 90 of deflectors 84 and cover structure is not required to close ports 44 to prevent reactant material from being expelled from those ports. The rotor is then braked to rapidly slow the rotor to further enhance mixing of the reactant materials and then successive photometric measurements are made along optical axis 94 while the rotor 10 is being spun at a speed of about 600 rpm. During the analytical run, centrifugal force drives all of the reactant material in each chamber 56, 58 radially outwardly of the deflector structure 84 and fills the analytical regions 34, the inner margins of the reactant materials (depending on their volumes) being located generally vertically as indicated in chain line 96 in FIGS. 5 and 6. Other types of analyses (for example, light scattering or fluorescence) can be made by directing radiation through end windows 28.

The rotor is a compact and mechanically and thermally stable structure which increases throughput and facilitates automated handling. The optimized shape of the analysis chamber regions provides enhanced optical path length (the analytical regions 34 have greater height than width) and permits analyses with reactant volumes in the range of 150–300 microliters without requiring covers for ports 42, 44.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the invention.

What is claimed is:

1. A multicuvette rotor for use in a centrifugal analyzer, said rotor defining a circumferential array of elongated radially extending cuvettes,
   each said elongated cuvette including structure defining a first chamber for receiving a first constituent and a loading port through which said first constituent is introduced into said first chamber region,
   structure defining a second chamber region for receiving a second constituent and a second loading port through which said second constituent is introduced into said second chamber region, divider structure between said first and second chamber regions, said divider structure having an inclined ramp surface and a crest portion spaced from the ceiling surface of said cuvette so that a transfer passage between said first and second chamber regions is defined between said crest portion and said ceiling surface of said cuvette through which said first constituent may be flowed into said second chamber region for forming a reaction product with said second constituent, deflector structure between said divider structure and said second loading port, said deflector structure extending downwardly from the ceiling surface of said cuvette into said transfer passage, a line extension of said ramp surface intersecting said ceiling surface of said cuvette radially inwardly from said deflector structure and said crest portion being substantially in alignment with the lower end of said deflector structure, and structure defining an analysis region adjacent the radially outer wall of said cuvette where said reaction product is subjected to analysis.

2. The rotor of claim 1 wherein said second chamber defining structure has generally vertical outwardly diverging sidewall surfaces in the vicinity of said deflector structure, said analysis region defining structure has generally vertical parallel sidewall surfaces, and further including inwardly converging generally vertical transition surfaces between said sidewall surfaces of said second chamber and said analysis region.

3. The rotor of claim 1 wherein the height of said ramp structure is greater than half the distance between said ceiling surface of said cuvette and the base of the cuvette.

4. The rotor of claim 1 wherein said ramp structure is inclined at an angle of less than 30° from the vertical.

5. The rotor of claim 1 wherein said deflector structure defines a channel extension of said second loading port.

6. The rotor of claim 5 wherein the outer surface portion of said channel extension adjacent said divider structure is of elliptical configuration.

7. The rotor of claim 1 wherein the length of said deflector structure is greater than one-fourth the distance between said ceiling surface of said cuvette and the base of the cuvette.

8. The rotor of claim 1 wherein said rotor has a diameter of about ten centimeters and an overall height of about one centimeter.

9. The rotor of claim 1 wherein said rotor defines thirty-nine analysis cuvettes and a reference position and includes a one-piece body member of transparent material that defines a circumferential array of elongated cuvette recesses, and a one-piece cover member of transparent material secured to said body member with a continuous seal extending around each said cuvette recess to define said circumferential array of analytical cuvettes.

10. The rotor of claim 9 wherein said body member in which said analysis regions are defined has a recessed annular optical window region, and said cover member is a disk that has a similar recessed annular optical window region adjacent its periphery that is aligned with said annular optical window recess in said body member.

11. The rotor of claim 10 wherein the height of said ramp structure is greater than half the distance between said ceiling surface of said cuvette and the base of the cuvette and the length of said deflector structure is greater than one-fourth the distance between said ceiling surface of said cuvette and the base of the cuvette.

12. The rotor of claim 1 and further including spacer projections in either the upper or lower surface of the rotor and an alignment recess in the periphery of the rotor so that a plurality of said rotors may be stacked in spaced angular alignment and the cuvettes maintained in stable thermal equilibrium by flow of equilibrating fluid over the spaced exterior surfaces of the rotors in the stack.

13. The rotor of claim 12 wherein said spacer projections are arcuate portions that project upwardly from the upper surface of said rotor, said rotor has a peripheral flange and two of said alignment recesses are in said flange and offset from diametrically opposite relation to one another by at least one cuvette.

14. The rotor of claim 12 wherein said deflector structure defines a channel extension of said second loading port that has an outer surface of elliptical configuration, said second chamber defining structure has generally vertical outwardly diverging sidewall surfaces in the vicinity of said deflector structure, said analysis region defining structure has generally vertical parallel sidewall surfaces, and further including inwardly converging generally vertical transition surfaces between the sidewall surfaces of said second chamber and said analysis region.

15. The rotor of claim 1 wherein each cuvette of said rotor has a length of about three centimeters, and its top and bottom walls are planar and spaced apart about ¾ centimeter in said analysis and second chamber regions and about 0.8 centimeter apart in said first chamber region.

16. The rotor of claim 15 wherein said rotor has a diameter of about ten centimeters and an overall height of about one centimeter, and said analysis region defining structure includes aligned annular optical recesses, each of which has an inner radius of about four centimeters, a width of about five millimeters and a planar base surface that is recessed about ¼ millimeter deep and has an optical finish better than three microinches, and inner surfaces of each said analysis region having similar optical quality while other surfaces of the cuvette compartments are rougher.

17. A multicuvette rotor for use in a centrifugal analyzer, said rotor defining a circumferential array of elongated radially extending cuvettes,
  each said elongated cuvette including structure defining a first chamber for receiving a first constituent and a loading port through which said first constituent is introduced into said first chamber region, structure defining a second chamber region for receiving a second constituent and a second loading port through which said second constituent is introduced into said second chamber region, divider structure between said first and second chamber regions that defines a transfer passage between said first and second chamber regions through which said first constituent may be flowed into said second chamber region for forming a reaction product with said second constituent, and structure defining an analysis region adjacent the radially outer wall of said cuvette where said reaction product is subjected to analysis, and
  spacer projection structure in at least one surface of said rotor so that a plurality of said rotors may be stacked in spaced alignment and the cuvettes maintained in stable thermal equilibrium by flow of equilibrating fluid over the spaced exterior surfaces of the rotors in the stack.

18. The rotor of claim 17 wherein said spacer projection structure includes spaced arcuate portions that project upwardly from the upper surface of said rotor.

19. The rotor of claim 17 and further including an alignment recess in the periphery of said rotor that permit a plurality of said rotors in said stack to be positioned in angular alignment.

20. The rotor of claim 19 wherein said rotor has a peripheral flange and two of said alignment recesses are in said flange and offset from diametrically opposite relation to one another by at least one cuvette.

21. The rotor of claim 17 and further including deflector structure between said divider structure and said second loading port, and said divider structure has an inclined ramp surface and a crest portion spaced from the ceiling surface of said cuvette so that said transfer passage is defined between said crest portion and said ceiling surface of said cuvette, said deflector structure extending downwardly from the ceiling surface of said cuvette into said transfer passage and a line extension of said ramp surface intersecting said ceiling surface of said cuvette radially inwardly from said deflector structure.

22. The rotor of claim 21 wherein said divider structure has a steeply inclined ramp surface with a crest height that is greater than half the distance between the upper and lower surfaces of the cuvette, and said deflector structure is a channel extension of said second loading port that has a smoothly curved outer surface and extends down from said ceiling surface a distance greater than one-fourth of the total height of said cuvette chamber in that region and the lower surface edge of said deflector structure is located substantially in alignment with said ramp crest.

23. The rotor of claim 22 wherein said first chamber has greater height than said second chamber, said second chamber defining structure has generally vertical outwardly diverging sidewall surfaces in the vicinity of said deflector structure, said analysis region defining structure has generally vertical parallel sidewall surfaces, and further including inwardly converging generally vertical transition surfaces between said sidewall surfaces of said second chamber and said analysis region.

24. The rotor of claim 23 wherein said rotor has a diameter of about ten centimeters and an overall height of about one centimeter, and said analysis region defining structure includes aligned annular optical recesses, each of which has an inner radius of about four centimeters, a width of about five millimeters and a planar base surface that is recessed about ¼ millimeter deep and has an optical finish better than three microinches, and inner surfaces of each said analysis region having similar optical quality while other surfaces of the cuvette compartments are rougher.

* * * * *